United States Patent
Dworak et al.

(10) Patent No.: US 12,286,495 B2
(45) Date of Patent: Apr. 29, 2025

(54) (METH)ACRYLATE-FUNCTIONALIZED WAXES AND CURABLE COMPOSITIONS MADE THEREWITH

(71) Applicant: Henkel AG & Co. KGaA, Duesseldorf (DE)

(72) Inventors: David Dworak, Middletown, CT (US); Deirdre Ledwith, Dublin (IE)

(73) Assignee: Henkel AG & Co. KGaA, Duesseldorf (DE)

(*) Notice: Subject to any disclaimer, the term of this patent is extended or adjusted under 35 U.S.C. 154(b) by 752 days.

(21) Appl. No.: 17/346,368

(22) Filed: Jun. 14, 2021

(65) Prior Publication Data

US 2022/0089800 A1 Mar. 24, 2022

Related U.S. Application Data

(63) Continuation of application No. PCT/EP2018/084819, filed on Dec. 13, 2018.

(51) Int. Cl.
| | | |
|---|---|---|
| C08F 222/22 | (2006.01) | |
| C07C 271/16 | (2006.01) | |
| C08F 220/36 | (2006.01) | |
| C09J 4/00 | (2006.01) | |
| C09J 133/14 | (2006.01) | |
| C09J 135/02 | (2006.01) | |

(52) U.S. Cl.
CPC ........ C08F 222/225 (2020.02); C07C 271/16 (2013.01); C08F 220/36 (2013.01); C08F 222/22 (2013.01); C09J 4/00 (2013.01); C09J 133/14 (2013.01); C09J 135/02 (2013.01); C08F 2800/20 (2013.01)

(58) Field of Classification Search
CPC .................................................. C08F 222/225
See application file for complete search history.

(56) References Cited

U.S. PATENT DOCUMENTS

| | | |
|---|---|---|
| 3,218,305 A | 11/1965 | Krieble |
| 4,180,640 A | 12/1979 | Doherty et al. |
| 4,250,322 A * | 2/1981 | Efimov .................... C08F 20/36 560/13 |
| 4,287,330 A | 9/1981 | Rich |
| 4,321,349 A | 3/1982 | Rich |
| 4,324,349 A | 4/1982 | Kaufman |
| 5,605,999 A | 2/1997 | Chu et al. |
| 5,811,473 A | 9/1998 | Ramos et al. |

(Continued)

FOREIGN PATENT DOCUMENTS

| | | |
|---|---|---|
| CN | 102558490 | 7/2012 |
| DE | 2365631 | 10/1975 |

(Continued)

OTHER PUBLICATIONS

International Search Report issued in connection with International Patent Application No. PCT/EP2018/057474 mailed on Jun. 1, 2018.

(Continued)

Primary Examiner — Michael F Pepitone
(74) Attorney, Agent, or Firm — Steven C. Bauman

(57) ABSTRACT

The present invention relates to (meth)acrylate-functionalized waxes and curable compositions, such as anaerobic adhesive compositions, made therewith.

9 Claims, 4 Drawing Sheets

(56) References Cited

U.S. PATENT DOCUMENTS

| | | | |
|---|---|---|---|
| 6,391,993 B1 | 5/2002 | Attarwala et al. | |
| 6,727,320 B2 | 4/2004 | Attarwala et al. | |
| 8,470,932 B2 | 6/2013 | Robinson et al. | |
| 2003/0171467 A1 | 9/2003 | Kneafsey et al. | |
| 2004/0170922 A1* | 9/2004 | Goto | B41M 5/368 |
| | | | 430/944 |
| 2005/0075411 A1 | 4/2005 | Wenning et al. | |
| 2007/0120925 A1 | 5/2007 | Belelie et al. | |
| 2011/0247521 A1 | 10/2011 | Robinson et al. | |
| 2012/0114898 A1 | 5/2012 | Kostick et al. | |
| 2012/0208965 A1 | 8/2012 | Joly et al. | |
| 2012/0232183 A1* | 9/2012 | Ooga | C08G 18/718 |
| | | | 522/144 |
| 2013/0014400 A1 | 1/2013 | Kucik et al. | |
| 2020/0048404 A1* | 2/2020 | Okada | C08G 18/73 |

FOREIGN PATENT DOCUMENTS

| | | | | |
|---|---|---|---|---|
| DE | 2365631 A * | 10/1975 | | C07C 271/06 |
| EP | 0 077 659 | 4/1983 | | |
| EP | 0 548 369 | 6/1993 | | |
| FR | 1581361 | 9/1969 | | |
| JP | 2005093377 | 4/2005 | | |
| JP | 2009075426 | 4/2009 | | |
| JP | 2022521449 A | 4/2022 | | |
| WO | 2004/024841 | 3/2004 | | |
| WO | 2016043241 | 3/2016 | | |
| WO | 2016/130503 | 8/2016 | | |
| WO | 2017068196 | 4/2017 | | |
| WO | WO-2018159758 A1 * | 9/2018 | | B29C 35/0805 |
| WO | 2020119908 A1 | 6/2020 | | |

OTHER PUBLICATIONS

R.D. Rich, "Anaerobic Adhesives" in Handbook of Adhesive Technology, 29, 467-79, A. Pizzi and K.L. Mittal, eds., Marcel Dekker, Inc., New York (1994).

* cited by examiner

(METH)ACRYLATE-FUNCTIONALIZED WAXES AND CURABLE COMPOSITIONS MADE THEREWITH

BACKGROUND

Field

The present invention relates to (meth)acrylate-functionalized waxes and curable compositions, such as anaerobic adhesive compositions, made therewith.

BRIEF DESCRIPTION OF RELATED TECHNOLOGY

Anaerobic adhesive compositions generally are well-known. See eg. R. D. Rich, "Anaerobic Adhesives" in *Handbook of Adhesive Technology*, 29, 467-79, A. Pizzi and K. L. Mittal, eds., Marcel Dekker, Inc., New York (1994), and references cited therein. Their uses are legion and new applications continue to be developed.

Conventional anaerobic adhesives ordinarily include a free-radically polymerizable acrylate ester monomer, together with a peroxy initiator and an inhibitor component. Often, such anaerobic adhesive compositions also contain accelerator components to increase the speed with which the composition cures.

Desirable anaerobic cure-inducing compositions to induce and accelerate cure may include one or more of saccharin, toluidines, such as N,N-diethyl-p-toluidine ("DE-p-T") and N,N-dimethyl-o-toluidine ("DM-o-T"), acetyl phenylhydrazine ("APH"), maleic acid, and quinones, such as napthaquinone and anthraquinone. See e.g. U.S. Pat. No. 3,218,305 (Krieble), U.S. Pat. No. 4,180,640 (Melody), U.S. Pat. No. 4,287,330 (Rich) and U.S. Pat. No. 4,321,349 (Rich).

Attempts have been made in the past to make adhesives, such as anaerobic ones, in a non-flowable form.

Thickeners have been added to adhesives to render them less flowable. But because other components in the adhesives are liquid the overall adhesive composition remains somewhat flowable and/or tacky. And the adhesive performance ordinarily does not reach its full performance potential because of the dilutive effect caused by the thickener.

For instance, U.S. Pat. No. 6,727,320 (Attarwala) is directed to and claims an adhesive composition comprising: at least one room-temperature flowable polymerizable compound; and b. a polymeric matrix selected from urea-urethanes, hydroxy or amine-modified aliphatic hydrocarbons, polyester-amide-based rheological additives and combinations thereof, and present in an amount sufficient to render the composition non-flowable at temperatures up to about 180° F. (82° C.) and where the composition is dispensable at room temperature without application of heat.

U.S. Patent Application Publication No. US 2003/0171467 (Kneafsey) is directed to a composition including (i) at least one anaerobically polymerizable compound; and (ii) at least one condensation product of an aldehyde and/or ketone with a polyol, where the composition is in the form of a soft-solid, for example in the form of a stick.

Curable adhesive tape products are known. One such example is available from Henkel Corporation, Rocky Hill, CT under the trade name Loctite® 249 Quicktape. This product consists of a liquid anaerobic threadlocker, sandwiched between two films of non-reactive polyamide/polyurethane film. See also U.S. Patent Application Publication No. US 2012/0114898.

Compositions, including those that are suitable for use in threadlocking applications, may be applied in a dry to the touch form with an anaerobic cure occurring subsequently.

In some cases a dry to the touch form may be achieved using a cure mechanism. For example a first cure mechanism may form the dry to touch form so as to hold the composition in place on an article while a second (e.g., anaerobic) cure mechanism may be activated later to achieve cure, say in a threadlocking application.

For example, European Patent No. 0 077 659 (Thompson) describes a pre-applied polymerizable fluid for sealing and locking engineering parts. The composition has two curing mechanisms in play. The first is UV light cure. An opacifier is dispersed in the fluid so that the fluid becomes substantially opaque to radiation. After the fluid is applied to one of the parts it is exposed to UV radiation whereupon a coating is formed, creating a surface layer which is a dry, tack-free crust. However, the subcutaneous fluid is unaffected by the radiation and remains in a generally liquid state. When the fluid-applied part (say a screw or a bolt) is threaded into another part (say a nut) the surface of the fluid layer breaks and the second polymerization (such as a free radical polymerization) is initiated and the second cure reaction takes place. The second polymerization mechanism acts to lock the threads together. Since in Thompson, only a skin is formed in the first polymerization and the remainder of the composition remains fluid below the skin, there is a risk that during handling of the coated parts the skin may be disrupted and the fluid composition may leak out.

European Patent No. 0 548 369 (Usami) describes a pre-applied adhesive composition for application to the threaded contact faces of a screw. The composition comprises a photo-hardening binder in which a secondary curable composition is dispersed. The secondary curable composition includes microencapsulated reactive monomer/activator/initiator.

International Patent Publication WO2004/024841 (Haller) describes curable compositions for application to a threaded article. The composition comprises a dispersion of (i) components of a first cure mechanism comprising: (a) a (meth)acrylate functional monomer component; (b) a (meth)acrylate functional oligomer component; and (c) a photoinitiator component; and (ii) components of a second cure mechanism comprising: (d) an amine component; and (e) an encapsulated epoxy resin component; together with (iii) a thickener component. The photoinitiator component is suitable upon irradiation of the composition to achieve a first cure through the depth of the composition applied to a threaded article so that a binder matrix is formed with the components of the second cure mechanism dispersed through the matrix.

An English language Abstract for Chinese patent publication No. CN 102558490 seemingly discloses a hot-meltable prepolymer, which is an urethane or polyurethane (meth)acrylate prepolymer with (meth)acryloyl terminal groups. The melting point of the prepolymer is 50-80° C. An anaerobic adhesive is prepared from the hot-meltable prepolymer, a monomer containing at least one acrylic ester group or methacryloyl group, a promoter, a stabilizer and an initiator. Liquid monomers are combined with the prepolymer to form a gel.

U.S. Pat. No. 8,470,932 is directed to a method of manufacturing a curable wax. The method of the '932 patent comprises: reacting a wax having a transformable functional group and a curable compound in the presence of an organic solvent to form curable wax, removing excess curable compound using hot water having a temperature of more than about 85° C., and solidifying the curable wax. In this method, excess curable compound is removed by performing by at least one extraction process using hot water, where during the extraction process excess curable compound is removed from a waxy phase into a water phase, and then the water phase is removed.

U.S. Patent Publication No. US2013/014400 describes urethane (meth)acrylate compositions that form a coating film asserted to be tack-free within 30 minutes. The composition comprises a urethane (meth) acrylate resin, a (meth) acrylate monomer, paraffin wax, and an ethylene-α-co-oligomer. The paraffin wax is added as a component that assists drying of a coating film, the paraffin wax stops evaporation of the (meth)acrylate monomer.

U.S. Patent Publication No. US2011/0247521 describes methods of manufacturing a curable wax, such as an acrylate of a hydroxyl-terminated polyethylene wax having the structure $CH_3$—$(CH_2)n$-$CH_2OH$, where n is from 22 to 24. The curable wax is formed via an esterification reaction of the hydroxyl-terminated polyethylene wax with acrylic acid. The curable wax is for use as a radiation curable ink.

U.S. Patent Publication No. US2007/0120925 similarly describes a curable wax by esterification of wax with acrylic acid. Radiation curable inks are formed by combining the curable wax with a curable monomer such as a (meth) acrylate.

International Patent Publication No. WO2016/130503 describes fluorine free fibrous treating compositions including isocyanate derived ethylenically unsaturated monomer containing oligomers. The composition includes one or more compounds derived from a reaction mixture that includes: (i) at least one isocyanate reactive oligomer comprising 2 to 20 repeating units; and (ii) at least one polyisocyanate; wherein the isocyanate reactive oligomer is made by the radical initiated reaction of a reaction mixture comprising at least one mercaptan and at least one (meth) acrylate monomer, wherein the at least one (meth)acrylate monomer comprises at least one isocyanate derived group and at least one hydrocarbon group having at least 16 carbon atoms. Such compositions are asserted to be useful for treating fibrous substrates to enhance their water repellency.

US Patent Publication No. US2005/0075411 describes light stable and weather stable coating films containing a powder coating composition containing from 30 to 98.5% by mass of a binder containing at least one urethane (meth) acrylate having a melting point of from 40 to 130° C.; from 1 to 20% by mass of at least one micronized wax and from 0.5 to 50% by mass of at least one auxiliary and/or at least one additive, the composition being cross-linked by actinic radiation. The coatings produced have a low gloss surface.

International Patent Application Publication No. WO2017/068198 describes anaerobically curable compositions comprising an anaerobically curable component that is a combination of a solid resin component and a solid anaerobically curable monomer. In some examples the solid resin component comprises (meth)acrylate functionalized polyester polyols, formed from semi-crystalline polyester polyols.

Notwithstanding the state of the art, it would be desirable to provide alternative anaerobically curable compositions that are suitable for provision into non-flowable forms, and particularly those which include a solid component that cures within the anaerobically curable composition.

SUMMARY

The present invention relates to (meth)acrylate-functionalized waxes and curable compositions, such as anaerobic adhesive compositions, made therewith.

The anaerobically curable compositions include a(meth) acrylate component; an anaerobic cure-inducing composition; and a (meth)acrylate-functionalized wax.

The (meth)acrylate-functionalized waxes may be formed from waxes having one or more hydroxyl groups that have been reacted with compounds containing at least one isocyanato group and at least one (meth)acrylate group. Under appropriate reaction conditions, the hydroxyl groups on the wax react with the isocyanato groups to form urethane linkages leaving the (meth)acrylate groups available to participate in a curing reaction with other constituents of the curable composition.

The (meth)acrylate-functionalized wax may be embraced by compounds having the formula:

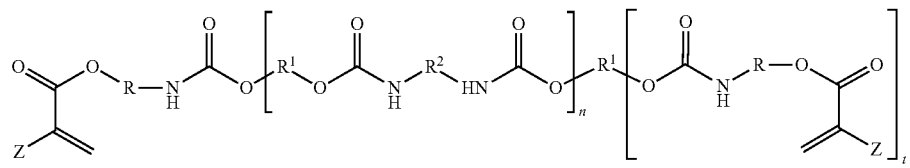

n is 0 to 3;

t is 1 to 4;

Z is H or Me;

R is a $C_2$-$C_{12}$ aliphatic group optionally substituted with one or more: $C_1$-$C_6$ alkyl, $C_1$-$C_6$ alkoxy, hydroxyl, acrylate, methacrylate, oxo and where said $C_2$-$C_{12}$ aliphatic group is optionally substituted with one or more heteroatoms selected from O, N or S;

$R^1$ comprises a $C_{10}$-$C_{20}$ aliphatic group optionally substituted with one or more $C_1$-$C_6$ alkyl groups, $C_1$-$C_6$ alkoxy, hydroxyl, oxo, carbonate, or one or more heteroatoms selected from O, N or S; and $R^2$ comprises a $C_2$-$C_{20}$ aliphatic group, a $C_5$-$C_{20}$ aryl group, or a $C_6$-$C_{20}$ alkaryl group optionally substituted with one or more $C_1$-$C_6$ alkyl, $C_1$-$C_6$ alkoxy, hydroxyl, and optionally substituted with one or more heteroatoms selected from O, N or S.

Suitably, R is $C_2$-$C_{12}$ alkyl, for example R may be ethyl, propyl, butyl, pentyl, hexyl or isomers thereof.

Desirably $R^1$ comprises a $C_{10}$-$C_{20}$ alkyl group optionally substituted with one or more $C_1$-$C_6$ alkyl groups, $C_1$-$C_6$ alkoxy, hydroxyl, oxo, carbonate, or one or more heteroatoms selected from O, N or S. For example $R^1$ may be a $C_{12}$-$C_{80}$ alkyl group.

$R^1$ may be $C_{18}$-$C_{40}$.

n is 0, 1 or 2, suitably n is 0 or 1; t may be 1, 2, 3 or 4; suitably t is 1 or 2.

Suitably, $R^1$ has the structure:

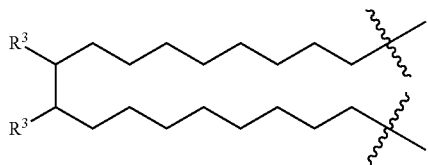

where each $R^3$ is $C_1$-$C_{12}$ alkyl.

For example, $R^1$ may have the following structure:

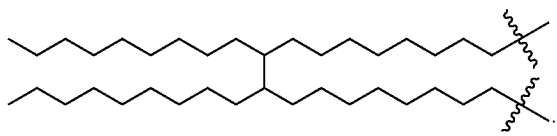 [SMILES: *CCCCCCCCC(CCCCCCCCC)C(CCCCCCCC*)CCCCCCCCC]

$R^1$ may have the following structure:

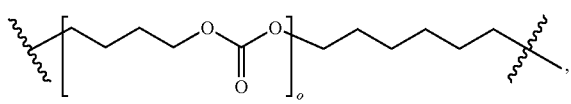

where o is from 15 to 30;
for example $R^1$ may be:

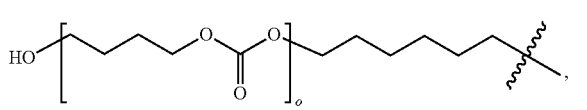

where o is from 15 to 25.

$R^1$ may have the following structure:

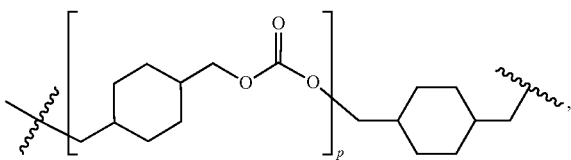

where p is from 10 to 30;
for example $R^1$ may be:

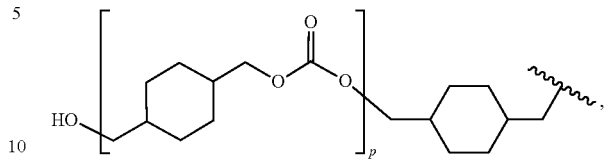

where p is from 15 to 25.

$R^2$ may be $C_2$-$C_{12}$ alkyl, for example $R^2$ may be ethyl, propyl, butyl, pentyl, hexyl, cyclopentyl, cyclohexyl, heptyl, octyl or isomers thereof.

$R^2$ may be

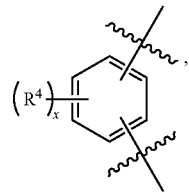

where x is 1-4 and each $R^4$ is independently selected from $C_1$-$C_6$ alkyl or $C_1$-$C_6$ alkoxy.

$R^2$ may be

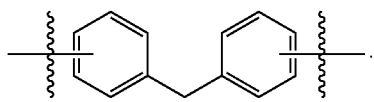

$R^2$ may be

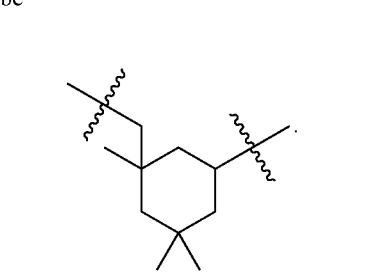

The compound may be selected from the group:
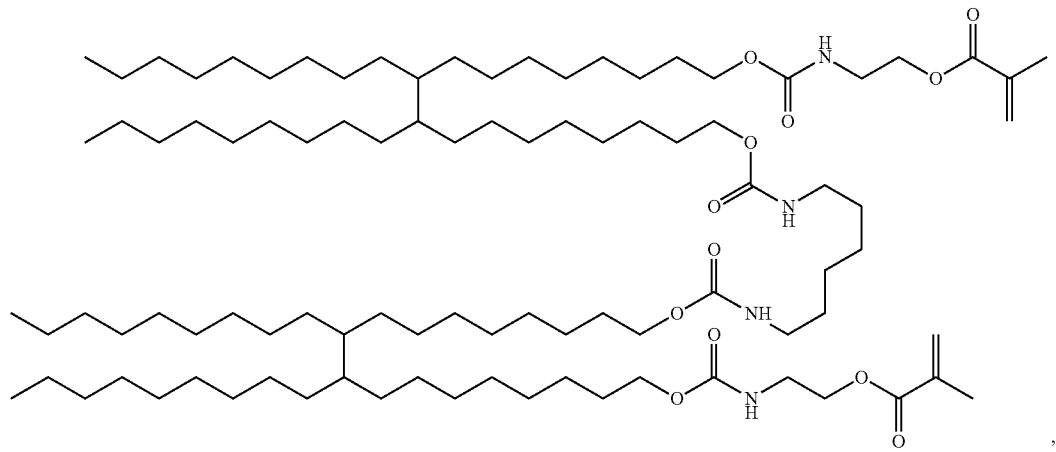
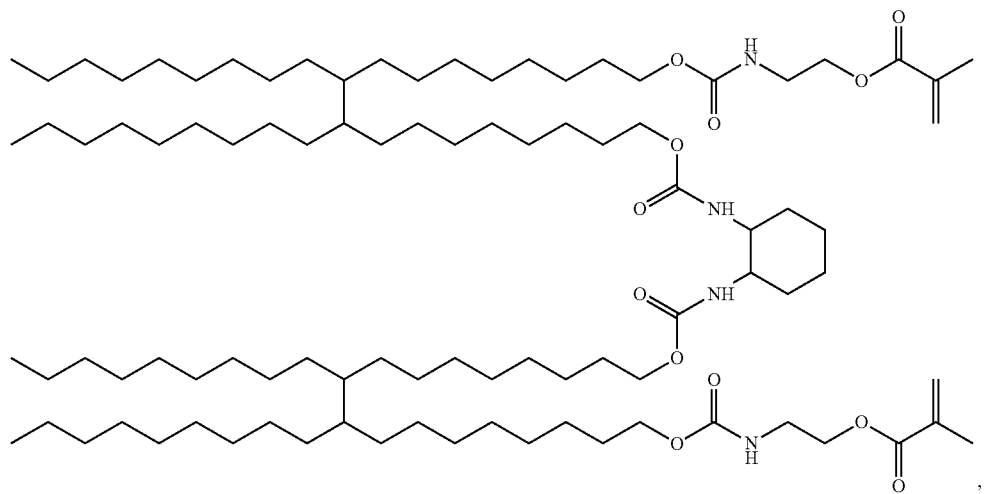
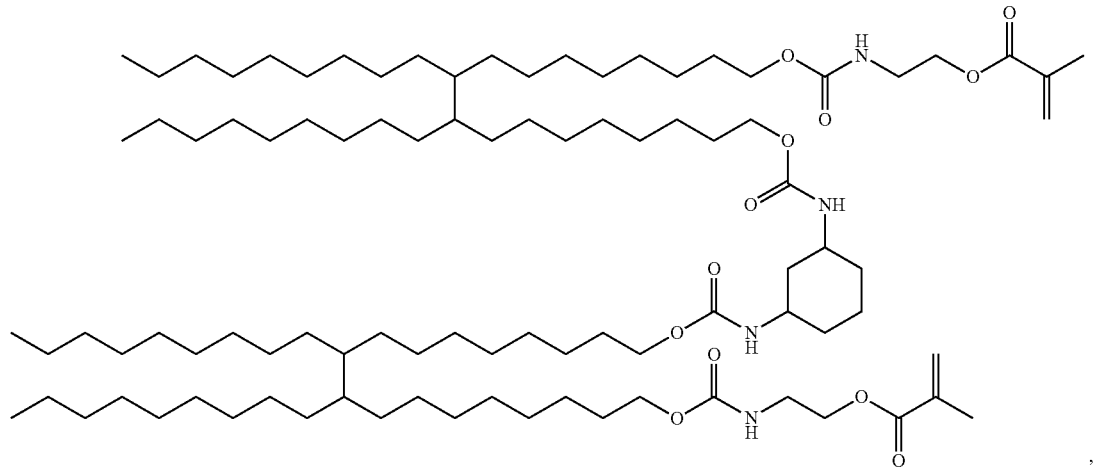

-continued

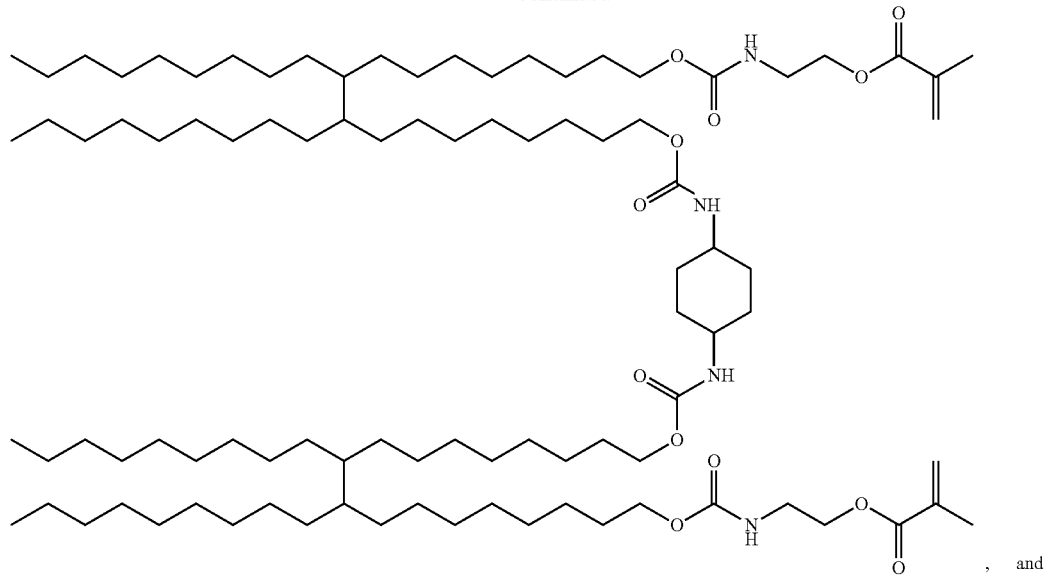

, and

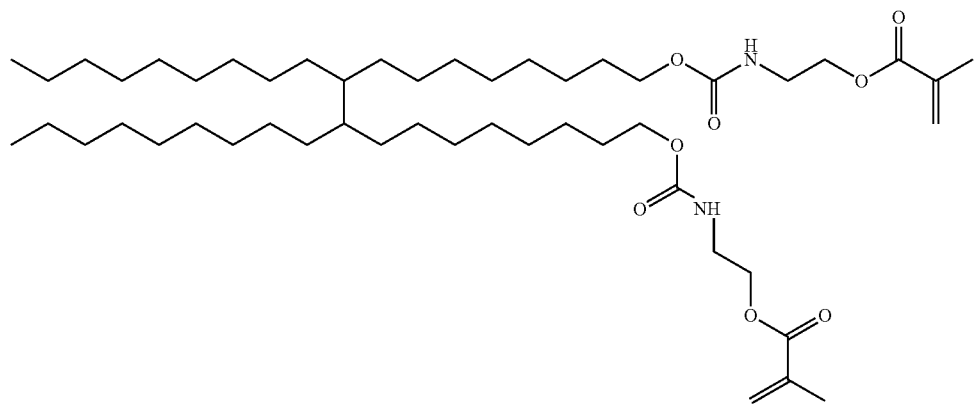

.

In another aspect the present invention provides an anaerobic curable composition comprising:
(a) a (meth)acrylate component;
(b) an anaerobic cure-inducing composition, and
(c) a compound as described herein.

Suitably, the anaerobic cure-inducing composition comprises a peroxide or hydroperoxide selected from the group consisting of cumene hydroperoxide, para-menthane hydroperoxide, t-butyl hydroperoxide, t-butyl perbenzoate, benzoyl peroxide, dibenzoyl peroxide, 1,3-bis(t-butylperoxylsopropyl)benzene, diacetyl peroxide, butyl 4,4-bis(t-butylperoxy)valerate, p-chlorobenzoyl peroxide, t-butyl cumyl peroxide, lauryl peroxide, urea-hydrogen peroxide, n-vinyl pyrrolidone-hydrogen peroxide, bis(tert-butylcyclohexyl peroxydicarbonate, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane, t-amyl hydroperoxide, 1,2,3,4-tertramethylbutyi hydroperoxide and combinations thereof.

Suitably, the compound of the invention is present in an amount of from about 10% by weight to about 60% by weight, based on the total weight of the composition, such as from about 25 to about 50% by weight, based on the total weight of the composition.

The cure-inducing component is typically present in an amount of from about 0.1 to about 10%, such as from about 1 to about 5%, for example about 5% by weight based on the total weight of the composition.

Advantageously, the cured compositions of the invention are substantially dry to touch and solvent free.

DETAILED DESCRIPTION

Figure 1:
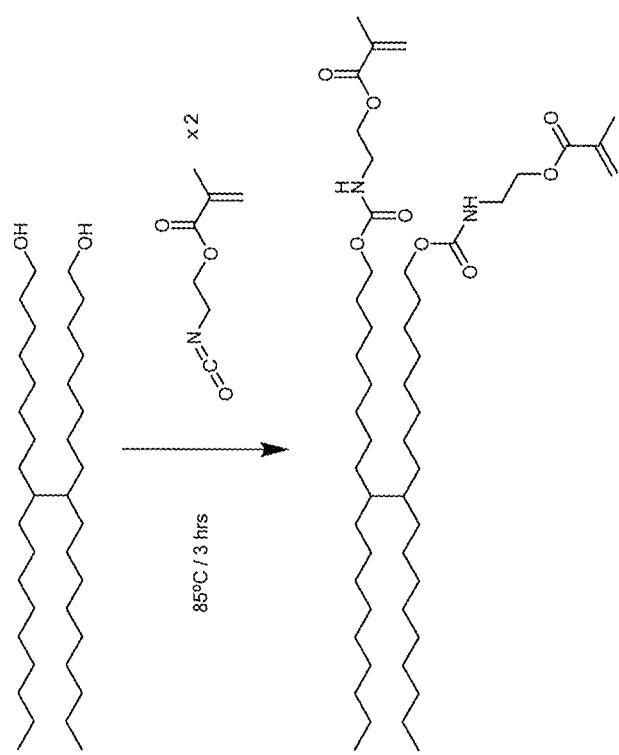
FIG. 1 depicts a synthetic scheme to make a (meth)acrylate-functional wax.

As outlined above, the present invention provides (meth)acrylate functionalised waxes represented by a compound having the formula:

[Structure diagram of (meth)acrylate-functionalized wax]

n is 0 to 3; t is 1 to 4; Z is H or Me;

R is a $C_2$-$C_{12}$ aliphatic group optionally substituted with one or more: $C_1$-$C_6$ alkyl, $C_1$-$C_6$ alkoxy, hydroxyl, acrylate, methacrylate, oxo and where said $C_2$-$C_{12}$ aliphatic group is optionally substituted with one or more heteroatoms selected from O, N or S;

$R^1$ comprises a $C_{10}$-$C_{120}$ aliphatic group optionally substituted with one or more $C_1$-$C_6$ alkyl groups, $C_1$-$C_6$ alkoxy, hydroxyl, oxo, carbonate, or one or more heteroatoms selected from O, N or S; and $R^2$ comprises a $C_2$-$C_{20}$ aliphatic group, a $C_5$-$C_{20}$ aryl group, or a $C_6$-$C_{20}$ alkaryl group optionally substituted with one or more $C_1$-$C_6$ alkyl, $C_1$-$C_6$ alkoxy, hydroxyl, and optionally substituted with one or more heteroatoms selected from O, N or S.

Significantly, the (meth)acrylate-functionalized waxes are solid or non-flowable at room temperature (about 20° C. to about 25° C.) and become flowable when exposed to an elevated temperature condition, such as at least about 30° C. to about 100° C., desirably about 40° C. to about 90° C., for example at about 80° C.

More specifically, the (meth)acrylate-functionalized waxes may be formed in one aspect from long chain aliphatic compounds bearing two or more hydroxyl groups. These long chain aliphatic compounds should be solid at room temperature and become flowable when exposed to an elevated temperature condition, about 30° C. to about 100° C., desirably about 40° C. to about 90° C., for example at about 85° C.

Ordinarily, the (meth)acrylate-functionalized waxes should return to a non-flowable or solid state in less than about 60 minutes, and remain curable for about 1 to about 5 months.

For instance, the (meth)acrylate-functionalized waxes may be formed from solid or highly viscous [e.g., greater than 3 cps @149° C. (ASTM D-3236)]hydroxyl group-containing compounds, such as lipids like fatty alcohols (or fatty acids—e.g., lauric ($C_{12}$), myristic ($C_{14}$), palmitic ($C_{16}$) and stearic ($C_{18}$)—having been reduced to form the counterpart straight-chain alcohols) or hydroxyl group-containing steroids (like cholesterol), hydroxyl-group containing terpenes, and hydroxyl-group containing bicyclic or tricyclic (fused, bridged or spiro) rings compounds.

Suitable examples of hydroxyl-terminated polyethylene waxes that may be functionalized with a (meth)acrylate group include compounds with the structure HO (CH$_2$)$_n$CH$_2$OH, where there may be one or more chain lengths, n, but the average chain length is in the range of about 16 to about 50, such as about 20 to about 30.

For example, hydroxyl-terminated compounds that may be functionalized with a (meth)acrylate group may have the formula:

[Structure diagram]

Where each $R^3$ is independently a $C_1$-$C_{12}$ aliphatic group, and each s is an integer in the range of from about 5 to about 30.

Suitably, each s is in the range of from 5 to 15, such as 6 or 7 or 8 or 9 or 10 or 11 or 12 or 13 or 14.

A hydroxyl-terminated wax suitable for forming a (meth)acrylate functionalized wax in accordance with the present invention may have the formula:

[Structure diagram]

where each $R^3$ is independently a $C_1$-$C_{12}$ alkyl group.

For example,

[Structure diagram]

Alternatively, a hydroxyl-terminated wax suitable for forming a (meth)acrylate functionalized wax in accordance with the present invention may have the formula:

[Structure diagram]

where o is in the range of from about 15 to about 35.

Suitably, o is in the range of from about 25 to about 30.

Alternatively, a hydroxyl-terminated wax suitable for forming a (meth)acrylate functionalized wax in accordance with the present invention may have the formula:

[Structure diagram]

where p is from 10 to 30.

Suitably, p is in the range of from about 12 to about 18.

Suitable commercially available examples of such waxes include UNILIN® 350 (hydroxyl functionalized wax), UNILIN® 425 (hydroxyl functionalized wax) and UNILIN® 550 (hydroxyl functionalized wax) with M, approximately equal to 375, 460, and 550 g/mol, respectively. UNILIN 700 (hydroxyl functionalized wax) may also be used. All of these waxes are commercially available from Baker-Petrolite. Guerbet alcohols, characterized as 2,2-dialkyl-1-ethanois, are also suitable choices. Suitable examples of Guerbet alcohols include those containing 16 to 36 carbons, many of which are commercially available from Jarchem Industries Inc., Newark, NJ. Another suitable choice is ISOFOL® 28, available commercially from Sasol North America Inc., Westlake, LA, which is 2-dodecylhexadecanol. PRIPOL® 2033 Dimerdiol (a C36 dimer diol mixture) available from Croda, Inc., New Castle, DE is another suitable commercially available choice. A further suitable choice is ETERNACOLL® UH-50 (polycarbonate diol wax), ETERNACOLL® UH-100 (polycarbonate diol wax) and ETERNACOLL® UH-200 (polycarbonate diol wax). ETERNACOLL® UC-100 (polycarbonate diol wax) may also be used.

The (meth)acrylate-functionalized waxes can be synthesized by the reaction of a wax having a hydroxyl functional group with a compound that provides a (meth)acrylate functional group. The wax having a hydroxyl functional group may be formed from a wax having a carboxyl functional group, which is reduced to the counterpart wax having a hydroxyl functional group.

Curable compositions, such as anaerobically curable ones, particularly well-suited for adhesive and sealant applications may be prepared with the (meth)acrylate-functionalized waxes.

Methods of making (meth)acrylate-functionalized waxes are provided too, where waxes having one or more hydroxyl groups may be reacted with compounds containing at least one isocyanato group and at least one (meth)acrylate group.

Anaerobic curable adhesive and sealant compositions generally are based on a (meth)acrylate component, together with an anaerobic cure-inducing composition. In the present invention, an additional component that is solid at room temperature and reactive with the (meth)acrylate component is added. Because this additional component is solid, it creates at least a highly viscous, if not outright solid at room temperature, curable composition. And because the additional solid component is reactive with the (meth)acrylate component, unlike known highly viscous or outright solid curable compositions whose increased viscosity was caused by components ordinarily unreactive with the (meth)acrylate component, the inventive curable compositions can reach performance levels unknown heretofore.

Thus, the anaerobically curable compositions include a (meth)acrylate component; an anaerobic cure-inducing composition; and a (meth)acrylate-functionalized wax.

The (meth)acrylate-functionalized waxes may be formed from waxes having one or more hydroxyl groups that have been reacted with compounds containing at least one isocyanato group and at least one (meth)acrylate group. Under appropriate reaction conditions, the hydroxyl groups on the wax react with the isocyanato groups to form urethane linkages leaving the (meth)acrylate groups available to participate in a curing reaction with other constituents of the curable composition.

The (meth)acrylate functionalized wax of the present invention is non-flowable or in the solid state at room temperature (25° C.).

For example, the (meth)acrylate functionalized wax compound having the formula:

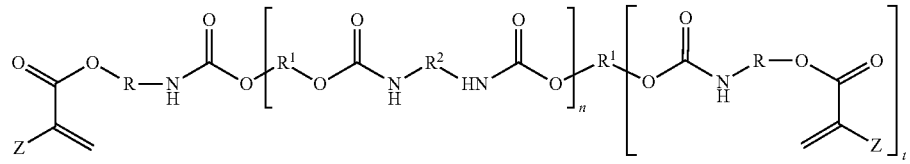

may be formed by the following reaction sequence:

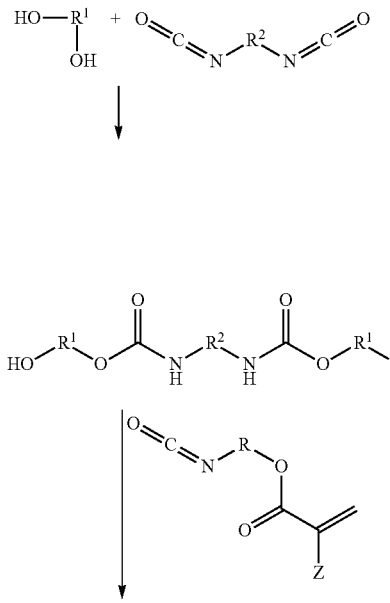

-continued

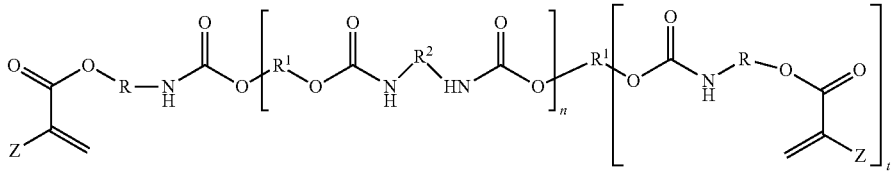

The skilled person will appreciate that alternative synthetic routes may be employed to synthesize the (meth)acrylate functionalized waxes of the present invention.

(Meth)acrylate monomers suitable for use as the (meth)acrylate component in the present invention may be selected from a wide variety of materials, such as those represented by $H_2C=CGCO_2R^8$, where G may be hydrogen, halogen or alkyl groups having from 1 to about 4 carbon atoms, and $R^8$ may be selected from alkyl, cycloalkyl, alkenyl, cycloalkenyl, alkaryl, alkaryl or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate, sulfone and the like.

Additional (meth)acrylate monomers suitable for use herein include polyfunctional (meth)acrylate monomers, for example di- or tri-functional (meth)acrylates such as polyethylene glycol di(meth)acrylates, tetrahydrofuran (meth)acrylates and di(meth)acrylates, hydroxypropyl (meth)acrylate ("HPMA"), hexanediol di(meth)acrylate, trimethylol propane tri(meth)acrylates ("TMPTMA"), diethylene glycol dimethacrylate, triethylene glycol dimethacrylates ("TRIEGMA"), tetraethylene glycol di(meth)acrylates, dipropylene glycol di(meth)acrylates, di-(pentamethylene glycol) di(meth)acrylates, tetraethylene diglycol di(meth)acrylates, diglycerol tetra(meth)acrylates, tetramethylene di(meth)acrylates, ethylene di(meth)acrylates, neopentyl glycol di(meth)acrylates, and bisphenol-A mono and di(meth)acrylates, such as ethoxylated bisphenol-A (meth)acrylate ("EBIPMA"), and bisphenol-F mono and di(meth)acrylates, such as ethoxylated bisphenol-A (meth)acrylate.

For example the anaerobically curable component may include (as an anaerobically curable monomer) Bisphenol A dimethacrylate:

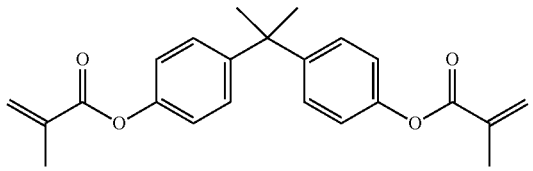 [SMILES: C=C(C)C(=O)Oc1ccc(C(C)(C)c2ccc(OC(=O)C(=C)C)cc2)cc1]

which has a melting point of approximately 72 to 74° C.

Still other (meth)acrylate monomers that may be used herein include silicone (meth)acrylate moieties ("SiMA"), such as those taught by and claimed in U.S. Pat. No. 5,605,999 (Chu), Incorporated herein by reference.

Other suitable monomers include polyacrylate esters represented by the formula

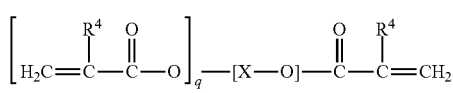

where $R^4$ is a radical selected from hydrogen, halogen or alkyl of from 1 to about 4 carbon atoms; q is an integer equal to at least 1, and preferably equal to from 1 to about 4; and X is an organic radical containing at least two carbon atoms and having a total bonding capacity of q plus 1. With regard to the upper limit for the number of carbon atoms in X, workable monomers exist at essentially any value. As a practical matter, however, a general upper limit is about 50 carbon atoms, such as desirably 30, and desirably about 20.

For example, X can be an organic radical of the formula:

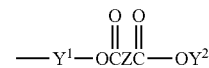

where each of $Y^1$ and $Y^2$ is an organic radical, such as a hydrocarbon group, containing at least 2 carbon atoms, and desirably from 2 to about 10 carbon atoms, and Z is an organic radical, preferably a hydrocarbon group, containing at least 1 carbon atom, and preferably from 2 to about 10 carbon atoms.

Other classes of useful monomers are the reaction products of di- or tri-alkylolamines (e.g., ethanolamines or propanolamines) with acrylic acids, such as are disclosed in French Pat. No. 1,581,361.

Examples of useful acrylic ester oligomers include those having the following general formula:

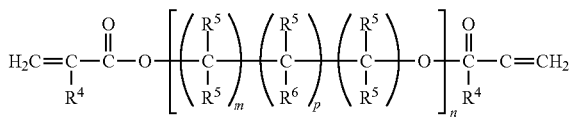

where $R^5$ represents a radical selected from hydrogen, lower alkyl of from 1 to about 4 carbon atoms, hydroxy alkyl of from 1 to about 4 carbon atoms, or

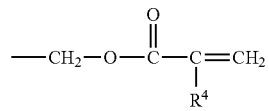

where $R^4$ is a radical selected from hydrogen, halogen, or lower alkyl of from 1 to about 4 carbon atoms; $R^e$ is a radical selected from hydrogen, hydroxyl, or

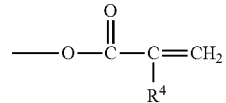

m is an integer equal to at least 1, e.g., from 1 to about 15 or higher, and desirably from 1 to about 8: n is an integer equal to at least 1, e.g., i to about 40 or more, and desirably between about 2 and about 10; and p is 0 or 1.

Typical examples of acrylic ester oligomers corresponding to the above general formula include di-, tri- and tetraethyleneglycol dimethacrylate; di(pentamethyleneglycol)dimethacrylate; tetraethyleneglycol diacrylate; tetraethyleneglycol di(chloroacrylate); diglycerol diacrylate; diglycerol tetramethacrylate; butyleneglycol dimethacrylate; neopentylglycol diacrylate; and trimethylolpropane triacrylate.

While di- and other polyacrylate esters, and particularly the polyacrylate esters described in the preceding paragraphs, can be desirable, monofunctional acrylate esters (esters containing one acrylate group) also may be used. When dealing with monofunctional acrylate esters, it is highly preferable to use an ester which has a relatively polar alcoholic moiety. Such materials are less volatile than low molecular weight alkyl esters and, more important, the polar group tends to provide intermolecular attraction during and after cure, thus producing more desirable cure properties, as well as a more durable sealant or adhesive. Most preferably, the polar group is selected from labile hydrogen, heterocyclic ring, hydroxy, amino, cyano, and halo polar groups. Typical examples of compounds within this category are cyclohexylmethacrylate, tetrahydrofurfuryl methacrylate, hydroxyethyl acrylate, hydroxypropyl methacrylate, t-butylaminoethyl methacrylate, cyanoethylacrylate, and chloroethyl methacrylate.

Another useful class of monomers is prepared by the reaction of a monofunctionally substituted alkyl or aryl acrylate ester containing an active hydrogen atom on the functional substituent. This monofunctional, acrylate-terminated material is reacted with an organic polyisocyanate in suitable proportions so as to convert all of the isocyanate groups to urethane or ureido groups. The monofunctional alkyl and aryl acrylate esters are preferably the acrylates and methacrylates containing hydroxy or amino functional groups on the non-acrylate portion thereof. Acrylate esters suitable for use have the formula

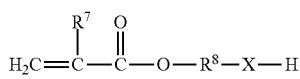

where X is selected from —O— and

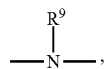

where $R^9$ is selected from hydrogen or lower alkyl of 1 through 7 carbon atoms; $R^7$ is selected from hydrogen, halogen (such as chlorine) or alkyl (such as methyl and ethyl radicals); and $R^8$ is a divalent organic radical selected from lower alkylene of 1 through 8 carbon atoms, phenylene and naphthylene. These groups upon proper reaction with a polyisocyanate, yield a monomer of the following general formula:

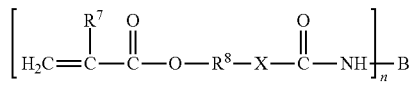

where n is an integer from 2 to about 6; B is a polyvalent organic radical selected from alkyl, alkenyl, cycloalkyl, cycloalkenyl, aryl, alkaryl, alkaryl and heterocyclic radicals both substituted and unsubstituted; and $R^7$, $R^8$ and X have the meanings given above.

Depending on the nature of B, these (meth)acrylate esters with urea or urethane linkages may have molecular weights placing them in the oligomer class (such as about 1,000 g/mol up to about 5,000 g/mol) or in the polymer class (such as about greater than 5,000 g/mol).

Desirably the anaerobically curable component comprises is chosen from at least one of epoxy (meth)acrylates, urethane (meth)acrylates, urethane di(meth)acrylates, alkyl (meth)acrylates, stearyl (meth)acrylates, isocyanurate (meth)acrylates, bisphenol-A-(meth)acrylates, ethoxylated bisphenol-A-(meth)acrylates, bisphenol-F-(meth)acrylates, ethoxylated bisphenol-F-(meth)acrylates, bisphenol-A di(meth)acrylates, ethoxylated bisphenol-A-di(meth)acrylates, bisphenol-F-di(meth)acrylates, and ethoxylated bisphenol-F-di(meth)acrylates.

For example the anaerobically curable component may include (as an anaerobically curable monomer) diisocyanates capped with hydroxyethyl methacrylate such as:

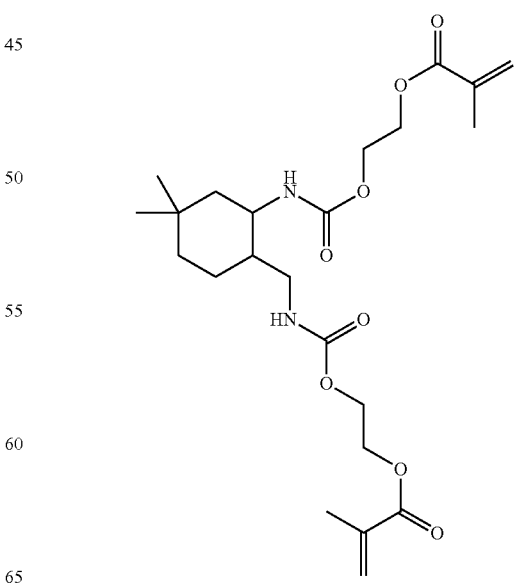

which is HEMA-IPDI-HEMA with a melting point of about 72-74° C.; or

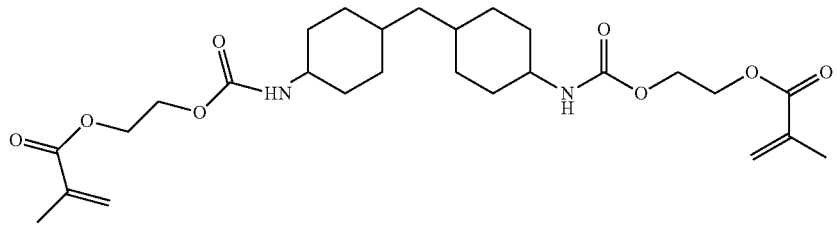 [SMILES: C=C(C)C(=O)OCCOC(=O)NC1CCC(CC2CCC(NC(=O)OCCOC(=O)C(=C)C)CC2)CC1]

which is HEMA-HMDI-HEMA with a melting point of about 75-85° C.; or

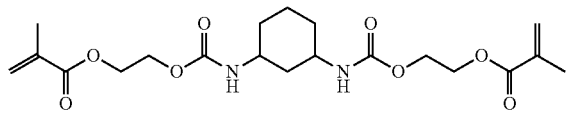 [SMILES: C=C(C)C(=O)OCCOC(=O)NC1CCCC(NC(=O)OCCOC(=O)C(=C)C)C1]

which is HEMA-1,3-CHDI-HEMA ("RRT600" in the Examples below) with a melting point of about 75-85° C.; or

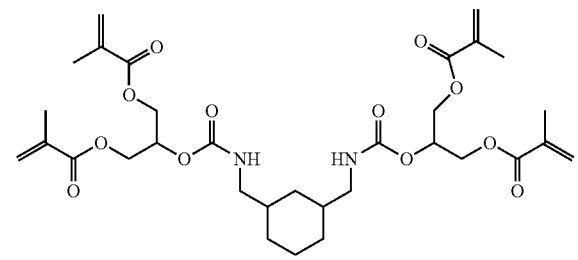 [SMILES: C=C(C)C(=O)OCC(COC(=O)C(=C)C)OC(=O)NCC1CCCC(CNC(=O)OC(COC(=O)C(=C)C)COC(=O)C(=C)C)C1]

which is Glycerol Dimethacrylate-6HXDI-Glycerol Dimethacrylate ("4RRT600" in the Examples below) with a melting point in the range from about 75 to about 85° C.

The proportions in which the reactants may be combined can be varied somewhat; however, it is generally preferred to employ the reactants in chemically equivalent amounts up to a slight excess.

Desirably, at least a portion of the (meth)acrylate component should be in the solid state at room temperature and particularly desirably capable of changing state from solid to liquid under elevated temperature conditions. For Instance, 2-methacryloxyethylphenylurethane—which is solid at room temperature—is a particularly desirable (meth)acrylate for use as at least a portion of the (meth)acrylate component, and indeed is used in the illustrative composition formulated in the Examples.

Of course, combinations of these (meth)acrylate monomers may also be used.

The (meth)acrylate component can comprise from about 10 to about 95% by weight of the composition, such as from about 20 to about 90%, or about 30 to about 85%, for example about 35 to about 80%, or from about 40 to about 75%, such as from about 60 to about 75% by weight, based on the total weight of the composition.

Additional components have in the past been included in traditional anaerobic adhesives to alter the physical properties of either the formulation or the reaction products thereof. For instance, one or more of maleimide components, thermal resistance-conferring co reactants, diluent components reactive at elevated temperature conditions, mono- or poly-hydroxyalkanes, polymeric plasticizers, and chelators (see U.S. Pat. No. 6,391,993, incorporated herein by reference) may be included to modify the physical property and/or cure profile of the formulation and/or the strength or temperature resistance of the cured adhesive.

When used, the maleimide, co-reactant, reactive diluent, plasticizer, and/or mono- or poly-hydroxyalkanes may be present in an amount within the range of about 1% to about 30% by weight, based on the total weight of the composition.

The anaerobic cure-inducing composition includes one or more of free radical initiators, free radical accelerators, and free radical stabilizers. Metal catalysts may also be used.

A number of well-known initiators of free radical polymerization are typically incorporated into anaerobic curable compositions including, without limitation, hydroperoxides, such as cumene hydroperoxide ("CHP"), para-menthane hydroperoxide, t-butyl hydroperoxide ("TBH") and t-butyl perbenzoate. Other peroxides include benzoyl peroxide, dibenzoyl peroxide, 1,3-bis(t-butylperoxyisopropyl)benzene, diacetyl peroxide, butyl 4,4-bis(t-butylperoxy)valerate, p-chlorobenzoyl peroxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane, t-amyl hydroperoxide, 1,2,3,4-tetramethylbutyl hydroperoxide and combinations thereof.

Encapsulated peroxides may also be used. For instance, encapsulated benzoyl peroxides may be used. Encapsulated benzoyl peroxide having a particle size of 200 um, commercially available from Japan Capsular Products is one particularly useful material. Others with particle sizes In the 100 um range are also desirable. Other than Japan Capsular Products, commercial sources of encapsulated benzoyl peroxides include Lipo Technologies Inc. and RT Dodge.

Such peroxides are typically employed in the present invention in the range of from about 0.1 to about 10% by weight, based on the total weight of the composition, with about 1 to about 5% by weight being desirable.

As noted, conventional accelerators of free radical polymerization are typically of the hydrazine variety (e.g., APH), as disclosed in U.S. Pat. No. 4,287,350 (Rich) and U.S. Pat. No. 4,321,349 (Rich). Maleic acid is usually added to APH-containing anaerobic cure inducing composition.

Co-accelerators of free radical polymerization may also be used in the compositions of the present invention including, without limitation, organic amides and imides, such as benzoic sulfimide (also known as saccharin) (see U.S. Pat. No. 4,324,349).

The accelerators (or co-accelerators) may be used in amounts of about 0.1 to about 5% by weight, such as about 1 to about 2% by weight, based on the total weight of the composition.

Stabilizers and inhibitors (such as phenols including hydroquinone and quinones) may also be employed to control and prevent premature peroxide decomposition and polymerization of the composition of the present invention Chelating agents [such as the tetrasodium salt of ethylenediamine tetraacetic acid ("EDTA")] may be used to trap trace amounts of metal contaminants. When used, chelating agents may ordinarily be present in the compositions in an amount from about 0.001% by weight to about 0.1% by weight, based on the total weight of the composition.

Other additives such as plasticizers, fillers, toughening agents (such as elastomers and rubbers) and other well-known additives may be incorporated therein where the art-skilled believes it would be desirable to do so.

The present invention also provides methods of preparing and using the inventive anaerobic adhesive and sealant compositions, as well as reaction products of the compositions.

The compositions of the present invention may be prepared using conventional methods which are well known to those persons of skill in the art. For instance, the components of the inventive anaerobic adhesive and sealant compositions may be mixed together in any convenient order consistent with the roles and functions the components are to perform in the compositions. Conventional mixing techniques using known apparatus may be employed.

The compositions of this invention may be applied to a variety of substrates to perform with the desired benefits and advantages described herein. For instance, appropriate substrates may be constructed from steel, brass, copper, aluminum, zinc, and other metals and alloys, ceramics and thermosets. An appropriate primer for anaerobic curable compositions may be applied to a surface of the chosen substrate to enhance cure rate. Or, the inventive anaerobic cure accelerators may be applied to the surface of a substrate as a primer. See e.g. U.S. Pat. No. 5,811,473 (Ramos).

The invention also provides a process for preparing a reaction product from the anaerobic curable composition of the present invention, the steps of which include applying the composition to a desired substrate surface and exposing the composition to an anaerobic environment for a time sufficient to cure the composition.

Advantageously the compounds of the invention are softer and have a lower melting range than prior art urethane functionalized (meth)acrylates. Furthermore, the compositions of the invention have increased lubricity in comparison to prior art compositions comprising urethane functionalized (meth)acrylates. This is particularly advantageous in a threadlocking application.

In view of the above description, it is clear that a wide range of practical opportunities are provided of which the following is for illustrative purposes only.

EXAMPLES

Synthesis of (Meth)Acrylate-Containing Wax

Example 1: To a 500 mL reaction kettle equipped with an overhead stirrer and nitrogen inlet/outlet was added 150.16 g (0.367 eq of OH) of hydroxyl functionalized wax (commercially available as UNILIN® 350). The kettle was heated to a temperature of 85° C. to allow the wax to melt. Once melted, 0.04 g of dibutyltin dilaurate was added with mixing. Next, 57.06 g (0.367 eq NCO) of 2-isocyanoethyl methacrylate was added with mixing under nitrogen for 3 hours. (See also FIG. 1.) The consumption of the NCO was verified with an FT-IR (2200 cm-1) and after 3 hours the NCO was completely reacted to yield a 100% methacrylated functionalized wax.

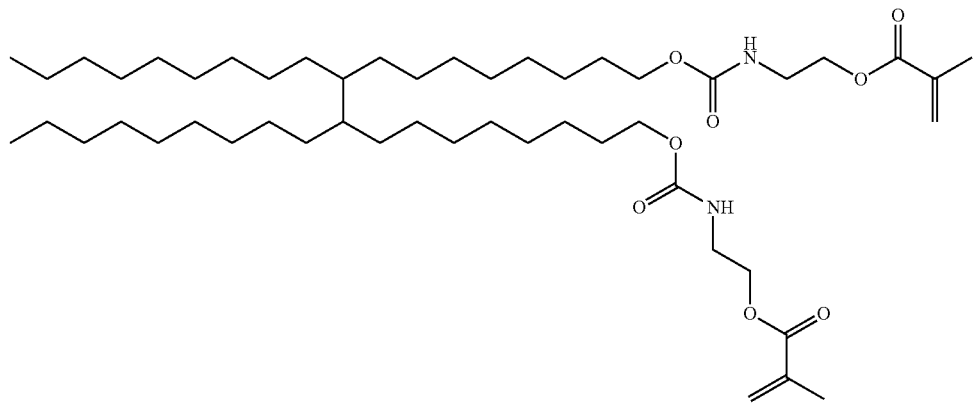 [SMILES: C=C(C)C(=O)OCCNC(=O)OCCCCCCCCC(CCCCCCCCC)C(CCCCCCCCC)CCCCCCCCOC(=O)NCCOC(=O)C(=C)C]

Synthesis Of Extended (Methylacrylate-containing Wax

Example 2: To a 500 mL reaction kettle equipped with an overhead stirrer and nitrogen inlet/outlet was added 114.80 g (0.281 eq of OH) of hydroxyl functionalized wax (commercially available as UNILIN 350). The kettle was heated to a temperature of 85° C. to allow the wax to melt. Once melted, 0.03 g of dibutyltin dilaurate was added with mixing. Next, 11.84 g (0.141 eq NCO) of hexane diisocyanate was added with mixing under nitrogen for 1 hour. Then, 20.74 g (0.134 eq NCO) of 2-isocyanoethyl methacrylate was added with mixing under nitrogen for 3 hours. The consumption of the NCO was verified with an FT-IR (2200 cm-1) and after 3 hours the NCO was completely reacted to yield an extended methacrylated functionalized wax.

Methacrylated and IPDI Extended Polycarbonate Diol Wax with 1,4-Butadiene Diol Hard Segments Example 3: To a 500 mL reaction kettle equipped with an overhead stirrer and nitrogen inlet/outlet was added 207.58 g (0.138 eq of OH) of a polycarbonate diol wax (commercially available as ETERNACOLL® UH-300) and 0.02 g of phosphoric acid. The kettle was heated with slow mixing to a temperature of 75° C. to allow the polycarbonate diol to melt. Once melted, 0.21 g of dibutyltin dilaurate and 0.69 g (0.015 eq of OH) of 1,4-butane diol were added with mixing. Next, 3.39 g (0.030 eq NCO) of isophorone diisocyanate was metered in with mixing under nitrogen and allowed to react for 1 hour. Then, 18.92 g (0.122 eq NCO) of 2-isocyanoethyl methacrylate was added with mixing under nitrogen for 3 hours. The consumption of the NCO was verified with an FT-IR (2200 cm-1) and after 3 hours the NCO was completely reacted to yield an methacrylated extended polycarbonate diol wax.

Methacrylated and HDI Extended Polycarbonate Diol Wax with 1,4-Butadiene Diol Hard Segments Example 4: To a 500 mL reaction kettle equipped with an overhead stirrer and nitrogen inlet/outlet was added 251.67 g (0.163 eq of OH) of a polycarbonate diol wax (commercially available as ETERNACOLL® UH-300) and 0.03 g of phosphoric acid. The kettle was heated with slow mixing to a temperature of 75° C. to allow the polycarbonate diol to melt. Once melted, 0.26 g of dibutyltin dilaurate and 1.87 g (0.042 eq of OH) of 1,4-butane diol were added with mixing. Next, 5.25 g (0.062 eq NCO) of hexamethylene diisocyanate was metered in with mixing under nitrogen and allowed to react for 1 hour. Then, 22.58 g (0.146 eq NCO) of 2-isocyanoethyl methacrylate was added with mixing under nitrogen for 3 hours. The consumption of the NCO was verified with an FT-IR (2200 cm-1) and after 3 hours the NCO was completely reacted to yield a methacrylated extended polycarbonate diol wax.

Methacrylated and HDI Extended Polycarbonate Diol Wax with 1,4-Butadiene Diol Hard Segments Example 5: To a 500 mL reaction kettle equipped with an overhead stirrer and nitrogen inlet/outlet was added 201.30 g (0.387 eq of OH) of a polycarbonate diol wax (commercially available as ETERNACOLL® UH-100) and 0.02 g of phosphoric acid. The kettle was heated with slow mixing to a temperature of 75° C. to allow the polycarbonate diol to melt. Once melted, 0.22 g of dibutyltin dilaurate and 4.36 g (0.097 eq of OH) of 1,4-butane diol were added with mixing. Next, 12.22 g (0.145 eq NCO) of hexamethylene diisocyanate was metered in with mixing under nitrogen and allowed to react for 1 hour. Then, 52.60 g (0.339 eq NCO) of 2-isocyanoethyl methacrylate was added with mixing under nitrogen for 3 hours. The consumption of the NCO was verified with an FT-IR (2200 cm-1) and after 3 hours the NCO was completely reacted to yield an methacrylated extended polycarbonate diol wax.

Methacrylated and IPDI Extended Polyester Diol Wax with 1,4-Butadiene Diol Hard Segments Example 6: To a 500 mL reaction kettle equipped with an overhead stirrer and nitrogen inlet/outlet was added 192.72 g (0.137 eq of OH) of a polyester diol wax (commercially available as PRIPLAST® 3172-SO-(GD)). The kettle was heated with slow mixing to a temperature of 75° C. to allow the polyester diol to melt. Once melted, 0.22 g of dibutyltin dilaurate and 1.54 g (0.034 eq of OH) of 1,4-butane diol were added with mixing. Next, 28.78 g (0.342 eq NCO) of isophorone diisocyanate was metered in with mixing under nitrogen and allowed to react for 1 hour. Then, 22.26 g (0.171 eq OH) of 2-hydroxyethyl methacrylate was added with mixing under nitrogen for 3 hours. The consumption of the NCO was verified with an FT-IR (2200 cm-1) and after 3 hours the NCO was completely reacted to yield an extended methacrylated polyester diol wax.

Preparation of an Anaerobic Curable Composition

Example 7: The following components listed in the table below were used to make anaerobic curable compositions for evaluation:

| Constituent | Amt/wt % |
|---|---|
| Di-functional methacrylated paraffinic wax[1] | 25.0 |
| 2-Methacryloxyethylphenylurethane | 34.5 |
| RRT600[2] | 34.5 |
| Anaerobic cure-inducing composition | 2.0 |
| BPO microcaps[3] | 4.0 |

[1]Prepared in the Example 1:

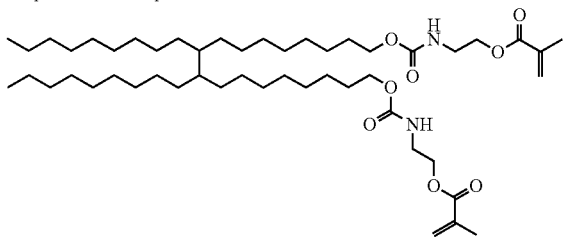

[2]RRT600 (HEMA-1,3-CHDI-HEMA):

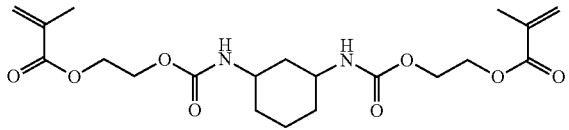 [SMILES: C=C(C)C(=O)OCCOC(=O)NC1CCCC(NC(=O)OCCOC(=O)C(=C)C)C1]

[3]Encapsulated benzoyl peroxide having a particle size of 200 um, commercially available from Japan Capsular Products.

Figure 2:
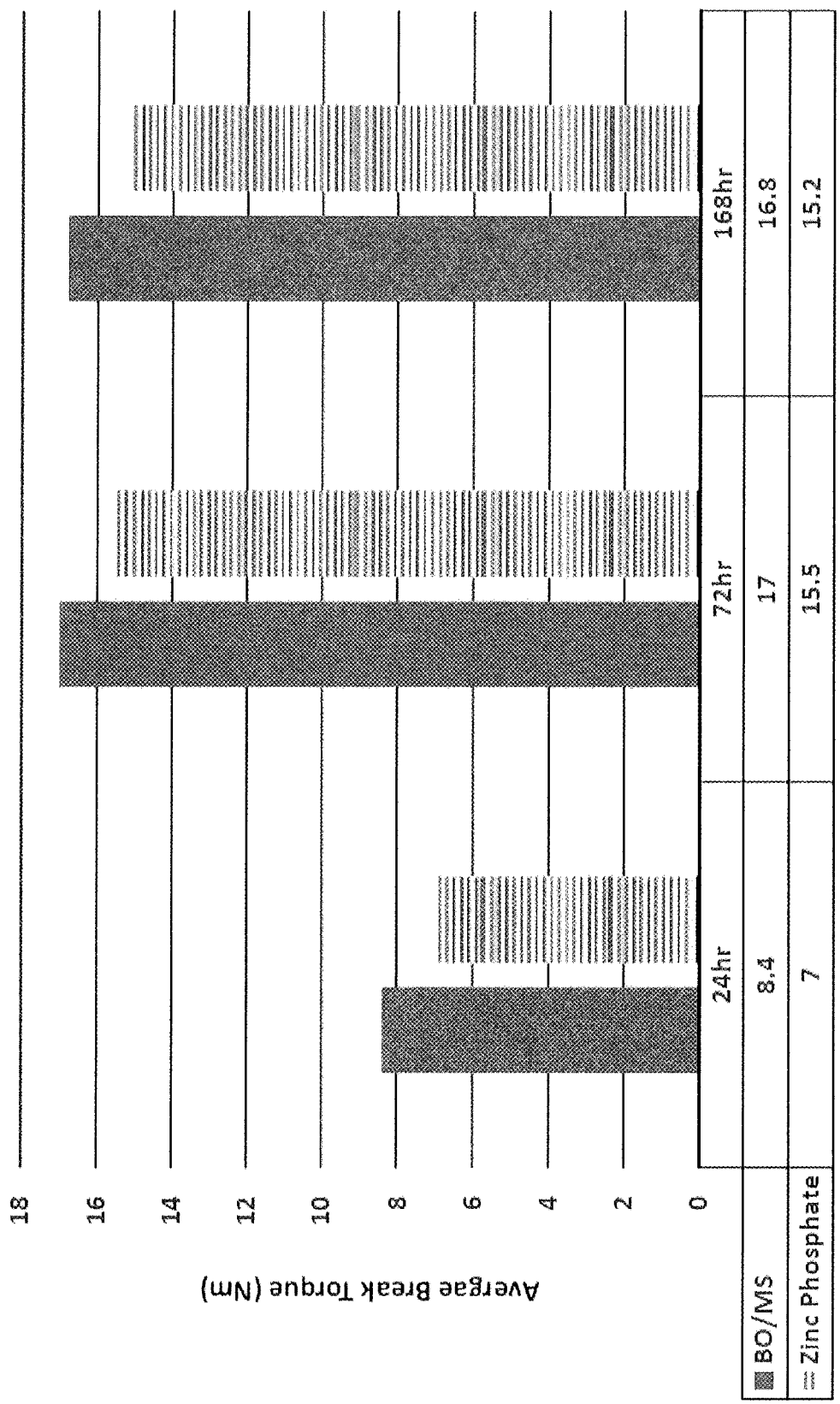
FIG. 2 depicts a bar chart showing performance over time on black oxide/mild steel substrates and zinc phosphate-coated steel substrates.

The formulation was applied to black oxide and mild steel substrates and zinc phosphate-coated steel substrates, and allowed to cure for periods of time ranging from 24 hours to 168 hours, as noted. After these time periods, break torque performance was measured and recorded. The measurements may be seen with reference to FIG. 2 and as captured in the table below:

| Substrates | Break Torque (Nm)/Time (hours) | | |
|---|---|---|---|
| | 24 | 72 | 168 |
| BO/MS | 8.4 | 17 | 16.8 |
| Zinc Phosphate | 7 | 15.5 | 15.2 |

Example 8: The following components listed in the table below were used to make anaerobic curable compositions for evaluation:

| Constituent | Amt/wt % |
| --- | --- |
| Di-functional methacrylated wax[4] | 35.01 |
| 2-Methacryloxyethylphenylurethane | 35.01 |
| RRT600 | 24.92 |
| Anaerobic cure-inducing composition | 0.61 |
| BPO microcaps | 4.45 |

[4]Prepared in Example 5.

The formulation was applied to black oxide and mild steel substrates, and allowed to cure for periods of time ranging from 24 hours to 168 hours, as noted. After these time periods, break torque performance was measured and recorded.

| Substrates | Break Torque (Nm)/Time (hours) 24 |
| --- | --- |
| BO/MS | 21.3 |

The average prevail for the composition of Example 8 was 7.1 N.m.

The break torque performance and prevail strengths were measured in accordance with ASTM D5649 "Torque Strength of Adhesives Used on Threaded Fasteners". Nuts and bolts were degreased prior to assembly with the formulations. The break strength is the initial torque required to break the bond when measured at the first movement between the nut and the bolt when unscrewing the assembly.

Suitably, the compositions of the invention have a minimum break torque strength on black oxide/mild steel or zinc phosphate as determined in accordance with ASTM D5649 of at least 15 N·m after 72 hours.

Differential Scanning Calorimetry (DSC)

Figure 3:
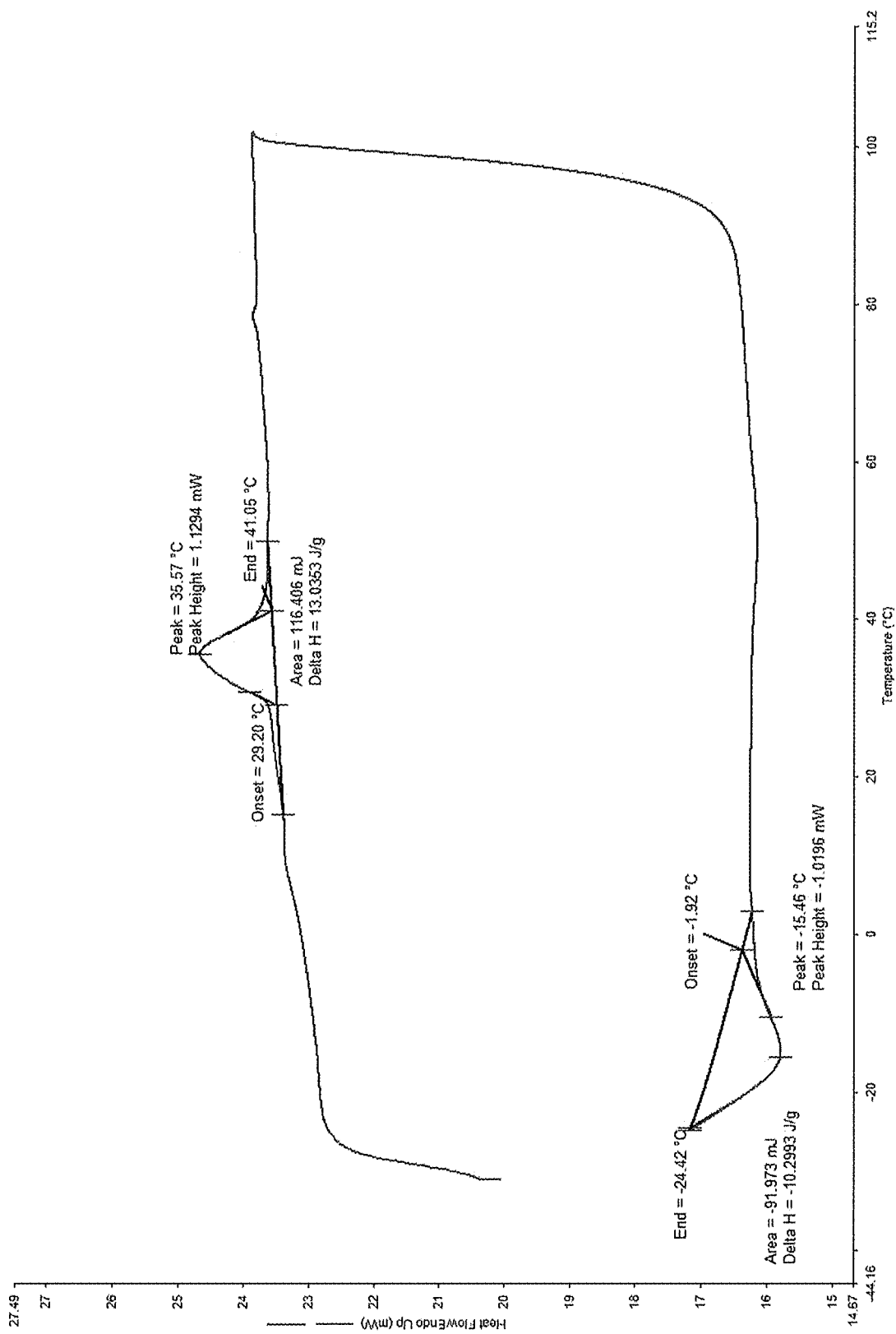
FIG. 3 shows a DSC thermogram for a compound of the invention.
Figure 4:
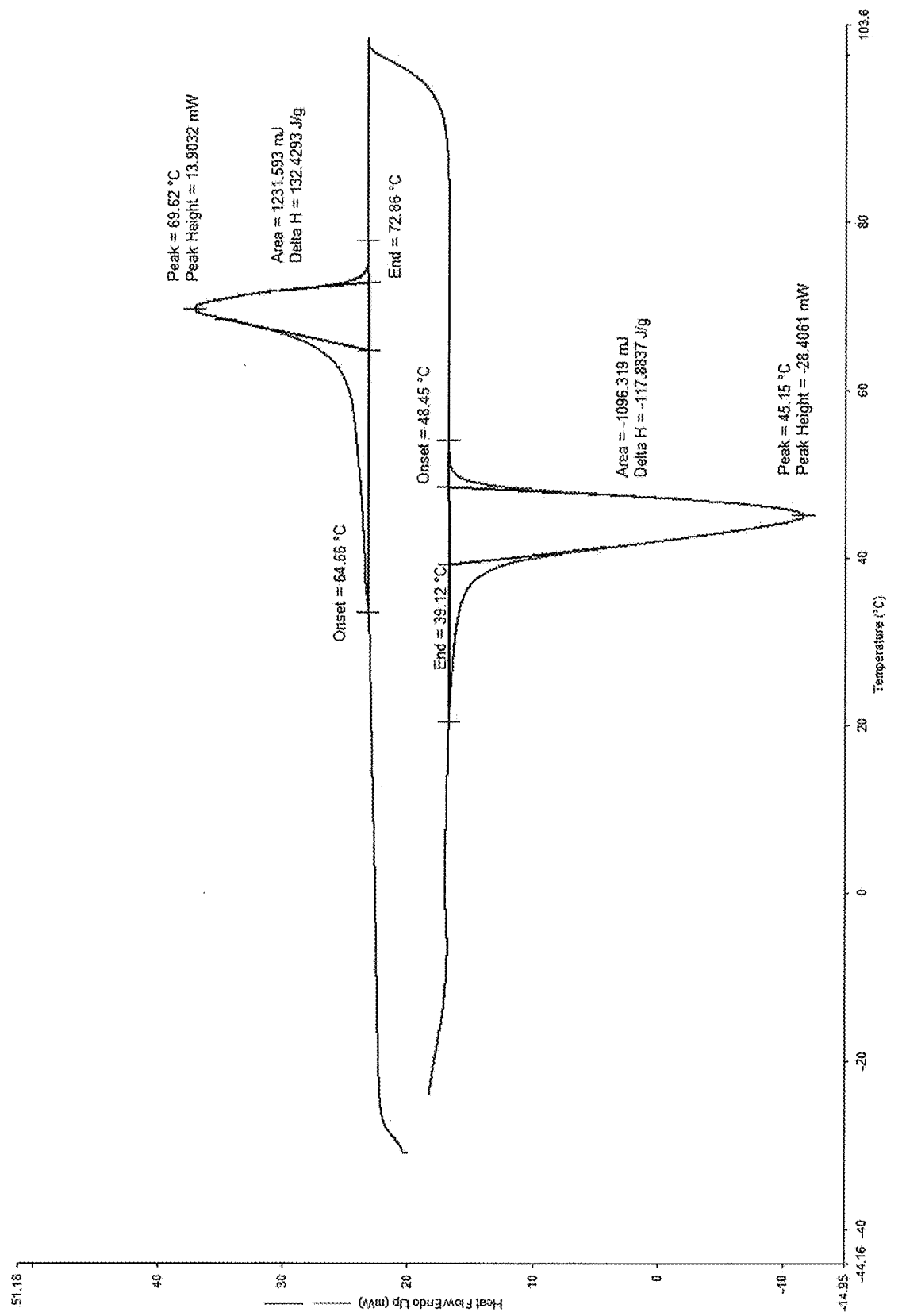
FIG. 4 shows a DSC thermogram for a prior art (meth)acrylate functionalized urethane.

Differential Scanning Calorimetry (DSC) can show the physical characteristics of the functionalised resins by determining their heat flux responses to changes in thermal conditions. Samples were analysed using a Perkin Elmer DSC 6000 according to ISO 11357-1:2016. Samples to be analysed were placed in amounts of 10-15 mg in aluminium pans and placed on a sample holder within the furnace. Thermograms obtained from the analysis show endothermic responses as an increase in mW and exothermic responses as a decrease in mW. Samples were heated from −30° C. to 100° C. at a rate of 10° C. per minute and then cooled to −20° C. at a rate of 10° C./min. The samples in FIG. 3 shows the thermogram for the urethane methacrylate functionalised wax resin from Example 3. FIG. 4 shows the thermogram for a urethane methacrylate functionalised semi-crystalline polyester resin. As can be seen in FIG. 4, the resin shows an endothermic melting with onset occurring at 64.6° C. and an exothermic recrystallisation occurring with a peak at 48.45° C. In contrast, the thermogram for the product of Example 3 in FIG. 3 shows a melting peak onset at 29.20° C. with no corresponding recrystallisation peak above 0° C. This shows that the product of Example 3 has a lower melting temperature than the resin in FIG. 3, in addition the product of Example 3 is a softer, amorphous material at room temperature as no recrystallisation occurs. Advantageously, such products can be used to make solid threadlocking compositions with increased lubricity.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A compound having a formula:

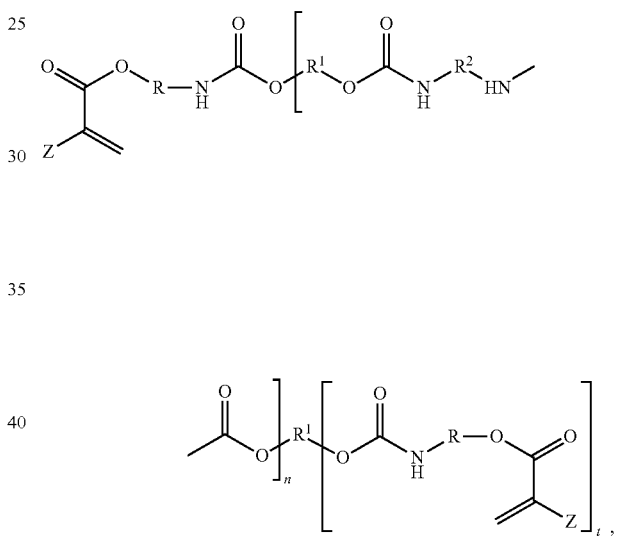

wherein n is 0 to 3; t is 1 to 4; Z is H or Me;

R is a $C_2$-$C_{12}$ aliphatic group optionally substituted with one or more: $C_1$-$C_6$ alkyl, $C_1$-$C_6$ alkoxy, hydroxyl, acrylate, methacrylate, oxo and where said $C_2$-$C_{12}$ aliphatic group is optionally substituted with one or more heteroatoms selected from O, N or S;

$R^1$ has the structure:

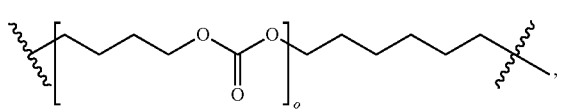

wherein o is from 15 to 30;

$R^2$ comprises a $C_2$-$C_{20}$ aliphatic group, a $C_5$-$C_{20}$ aryl group, or a $C_6$-$C_{20}$ alkaryl group optionally substituted with one or more $C_1$-$C_6$ alkyl, $C_1$-$C_6$ alkoxy, hydroxyl, and optionally substituted with one or more heteroatoms selected from O, N or S.

2. A compound having a formula:

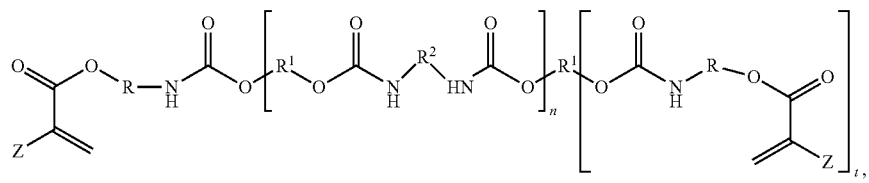

wherein n is 0 to 3; t is 1 to 4; Z is H or Me;
R is a $C_2$-$C_{12}$ aliphatic group optionally substituted with one or more: $C_1$-$C_6$ alkyl, $C_1$-$C_6$ alkoxy, hydroxyl, acrylate, methacrylate, oxo and where said $C_2$-$C_{12}$ aliphatic group is optionally substituted with one or more heteroatoms selected from O, N or S;
$R^1$ has the structure:

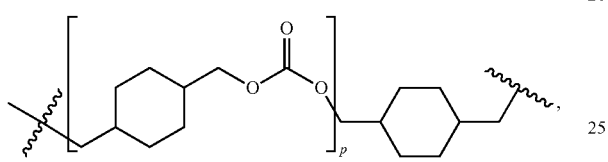

wherein p is from 10 to 30;

$R^2$ comprises a $C_2$-$C_{20}$ aliphatic group, a $C_5$-$C_{20}$ aryl group, or a $C_5$-$C_{20}$ alkaryl group optionally substituted with one or more $C_1$-$C_6$ alkyl, $C_1$-$C_6$ alkoxy, hydroxyl, and optionally substituted with one or more heteroatoms selected from O, N or S.

3. A compound having a structure selected from:

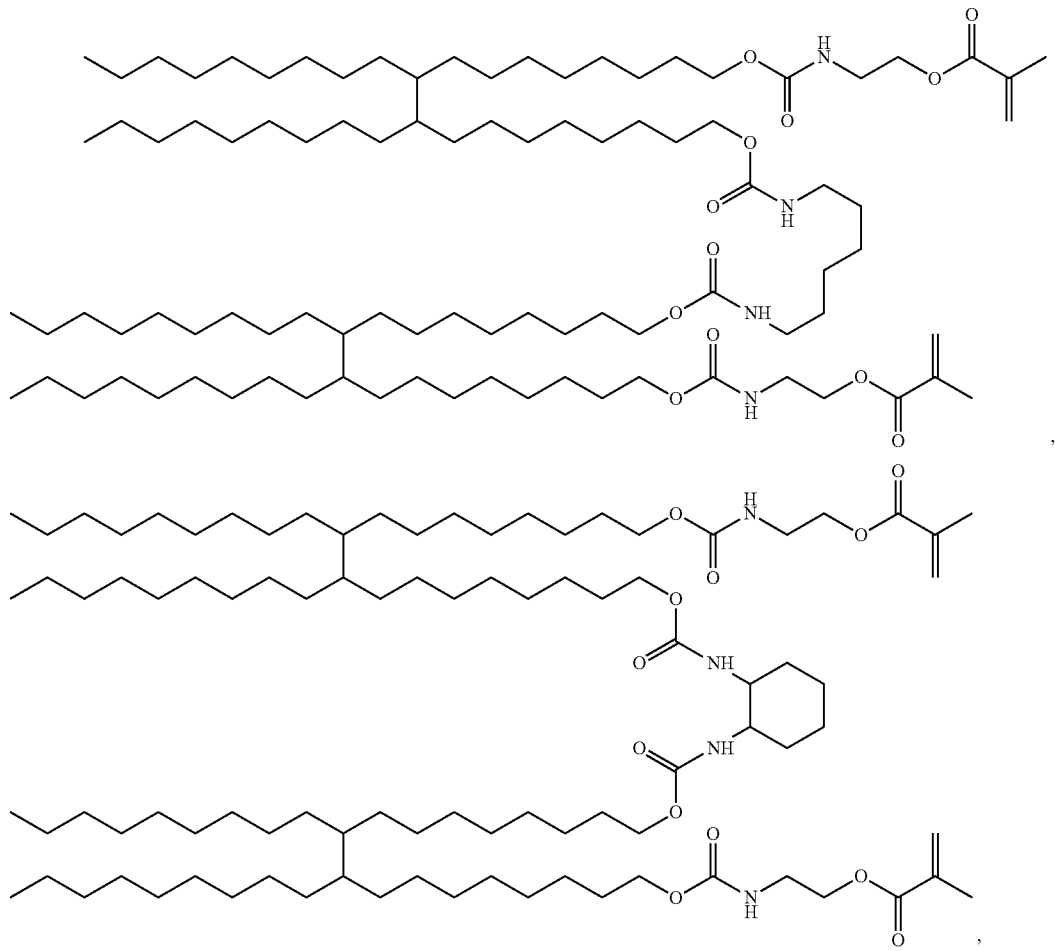

-continued

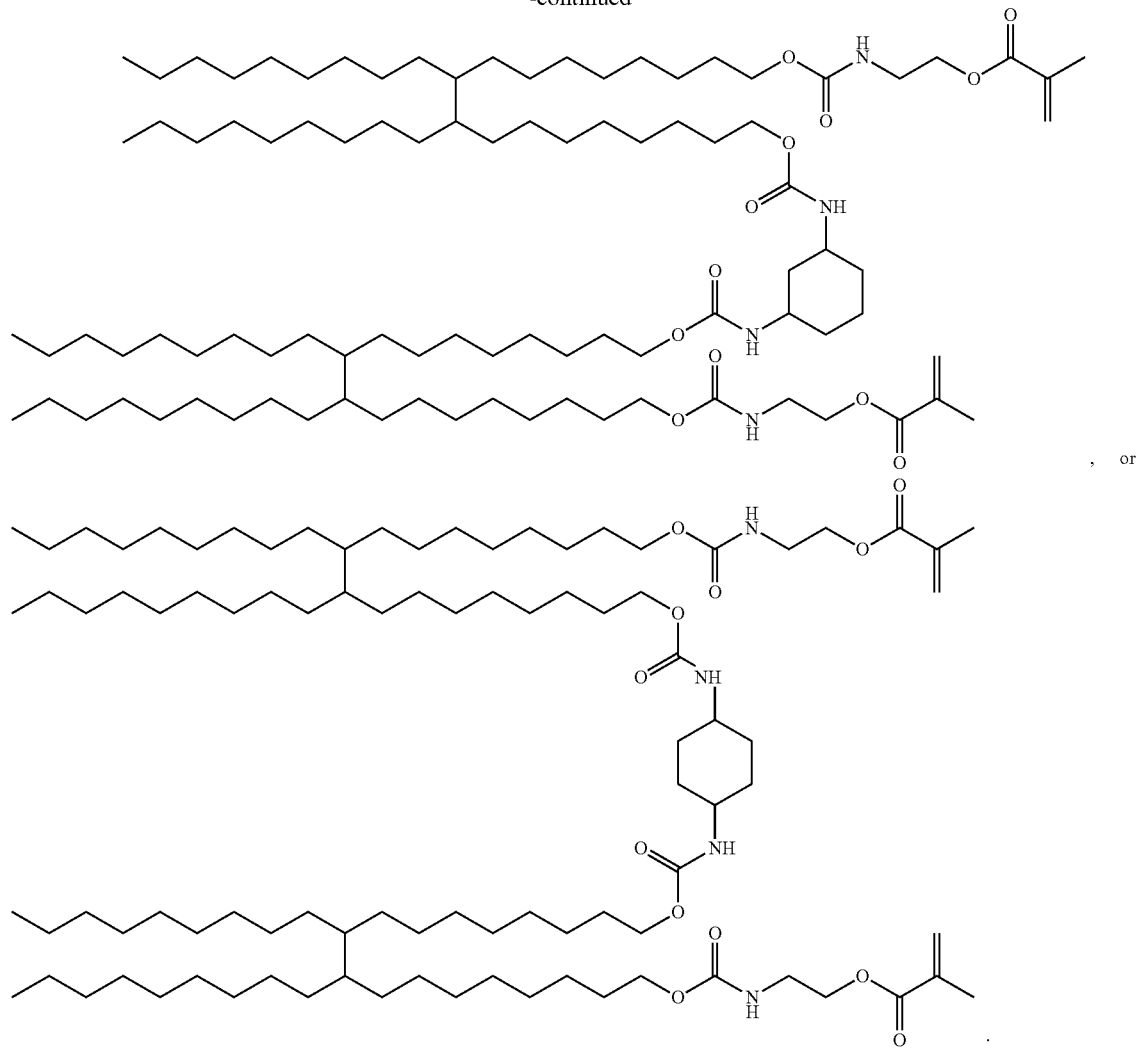

, or

4. An anaerobic curable composition comprising:
(a) a (meth)acrylate component;
(b) an anaerobic cure-inducing composition; and
(c) a compound according to claim 1.

5. The anaerobic curable composition of claim 4, wherein the anaerobic cure-inducing composition comprises a peroxide or hydroperoxide selected from the group consisting of cumene hydroperoxide, para-menthane hydroperoxide, t-butyl hydroperoxide, t-butyl perbenzoate, benzoyl peroxide, dibenzoyl peroxide, 1,3-bis(t-butylperoxyisopropyl) benzene, diacetyl peroxide, butyl 4,4-bis(t-butylperoxy) valerate, p-chlorobenzoyl peroxide, t-butyl cumyl peroxide, lauryl peroxide, urea-hydrogen peroxide, n-vinyl pyrrolidone-hydrogen peroxide, bis(tert-butylcyclohexyl peroxydicarbonate, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane, t-amyl hydroperoxide, 1,2,3,4-tetramethylbutyl hydroperoxide and combinations thereof.

6. The anaerobic curable composition of claim 4, wherein the compound is present in an amount of from about 10% by weight to about 60% by weight by weight based on the total weight of the composition.

7. The anaerobic curable composition of claim 4, wherein the compound is present in an amount of from about 25% by weight to about 50% by weight based on the total weight of the composition.

8. An anaerobic curable composition comprising:
(a) a (meth)acrylate component;
(b) an anaerobic cure-inducing composition; and
(c) a compound according to claim 2.

9. An anaerobic curable composition comprising:
(a) a (meth)acrylate component;
(b) an anaerobic cure-inducing composition; and
(c) a compound according to claim 3.

* * * * *